(12) United States Patent
Nelles et al.

(10) Patent No.: US 7,041,343 B1
(45) Date of Patent: May 9, 2006

(54) METHOD FOR PROVIDING A SUBSTRATE STRUCTURE FOR ORIENTED NEURITE OUTGROWTH, SUBSTRATE STRUCTURE, AND DEVICE FOR MONITORING NEURON

(75) Inventors: Gabriele Nelles, Stuttgart (DE); Akio Yasuda, Stuttgart (DE)

(73) Assignee: Sony International (Europe) GmbH, Berlin (DE)

( * ) Notice: Subject to any disclaimer, the term of this patent is extended or adjusted under 35 U.S.C. 154(b) by 0 days.

(21) Appl. No.: 09/744,113

(22) PCT Filed: May 18, 2000

(86) PCT No.: PCT/EP00/04517

§ 371 (c)(1),
(2), (4) Date: Mar. 19, 2001

(87) PCT Pub. No.: WO00/71677

PCT Pub. Date: Nov. 30, 2000

(30) Foreign Application Priority Data

May 19, 1999 (EP) .................................. 99109853

(51) Int. Cl.
*C09K 19/56* (2006.01)
(52) U.S. Cl. ................. 428/1.1; 428/1.2; 428/473; 607/50
(58) Field of Classification Search ............ 428/1.2, 428/1.25–1.27, 1.33, 1.62, 475.2, 473; 607/50; 600/546, 554; 128/898
See application file for complete search history.

(56) References Cited

U.S. PATENT DOCUMENTS

| | | | |
|---|---|---|---|
| 3,864,021 A | | 2/1975 | Katagiri et al. ........ 350/160 LC |
| 4,857,227 A | * | 8/1989 | Adams et al. .......... 252/299.65 |
| 5,486,403 A | * | 1/1996 | Ishitaka et al. .............. 428/167 |
| 5,510,628 A | | 4/1996 | Georger, Jr. et al. ........... 257/32 |
| 5,686,549 A | * | 11/1997 | Grainger et al. .............. 528/25 |
| 6,061,113 A | * | 5/2000 | Kawata ...................... 349/117 |

FOREIGN PATENT DOCUMENTS

| | | |
|---|---|---|
| EP | 0 402 718 | 12/1990 |
| EP | 0 887 667 | 12/1998 |

OTHER PUBLICATIONS

Yasuhiko Jimbo et al: "Electrical Stimulation of Cultured Neutral Cells by Planar Electrode Array" Proceedings of the Annual Conference of the Engineering in Medicine and Biology Society, US, New York, IEEE, vol. Conf. 12, p. 1741-1742, XP000239375.

(Continued)

*Primary Examiner*—Harold Pyon
*Assistant Examiner*—Sow-Fun Hon
(74) *Attorney, Agent, or Firm*—Frommer Lawrence & Haug LLP; William S. Frommer

(57) ABSTRACT

The invention relates to a method for providing a substrate structure for oriented neurite outgrowth, wherein a basic substrate is provided, characterized in that at least one alignment layer is deposited on said substrate and a mono- or multi-layer of a liquid crystal material is deposited on said at least one alignment layer or a combined alignment layer is deposited on said substrate, thereby providing a structured surface.

23 Claims, 3 Drawing Sheets

OTHER PUBLICATIONS

Yasuhiko Kimbo et al: "Simultaneous Measurement of Intracellular Calcium and Electrical Activity From Patterned Neural Networks in Culture" IEEE Transactions on Biomedical Engineering, US, IEEE, Inc. New York, vol. 40, No. 8, p. 804-810, XP000418557.

Kleinfeld D et al: "Controlled Outgrowth of Dissociated Neurons on Patterned Substrates", J Neurosci, vol. 8, No. 11, 1988, pp. 4098-4120, XP000915297.

Patent Abstracts of Japan, vol. 0185, No. 22, Sep. 30, 1994, JP 06 180455, Jun. 28, 1994.

* cited by examiner

METHOD FOR PROVIDING A SUBSTRATE STRUCTURE FOR ORIENTED NEURITE OUTGROWTH, SUBSTRATE STRUCTURE, AND DEVICE FOR MONITORING NEURON

BACKGROUND OF THE INVENTION

This application is a 371 of PCT/EP00/04517 filed May 18, 2000.

The present invention is related to a method for providing a substrate structure for oriented neurite outgrowth as well as to the respective substrate structure itself. The present invention is further related to a device for monitoring cell or neuron activity, comprising a substrate, at least one electronic device and at least one neuron or cell coupled with said electronic device.

During the past decades there has been a growing interest in the development of experimental systems, in which a small number of neurons are grown in defined patterns. It is a goal to provide a neuro-electronic system to investigate the structure-function relation of neural architectures.

Individual neurons can be stimulated and the electric activity and/or changes in membrane potential of neurons can be recorded and investigated.

The technological products and outputs arising from such investigations and respective devices will be especially the design of test systems for pharmaceutical development, prosthetic devices and neural network engineering.

Very important for the above-mentioned products and investigations is the physical interfacing, i.e. an extremely close contact of the nerve cells or neurons with the artificial substrate, especially to achieve the desired coupling between individual neurons and e.g. respective monitoring devices.

Regarding the physical interfacing, interactions of cultured neurons with defined surfaces are of a very high importance. The control of the function and geometric patterns of neurons in vitro, i.e. in an artificial environment, is dependent on the interaction of the cells with the culture substrate.

In order to avoid biosystems to denature in contact with the artificial substrate surfaces it is known to first treat substrate surfaces with biological relevant substances to improve neuronal survival. Peptide polymers, e.g. polylysine (PL) with pendent ε-amine groups are suggested as substrate materials for many types of neurons in culture, see e.g. "Interfacing Neurons and Silicon by Electrical Induction", P. Fromherz, Ber. Bunsenges. Phys. Chem. 1996, 100, 1093–1102.

It is further known to use self-assembled monolayers to create artificial surfaces for in vitro neuronal culture. Chemical functional groups can be incorporated into silane or thiol molecules used for self-assemby, see book of D. Stenger and T. McKenna, "Enabling Technologies for Cultured Neural Networks", Academic Press, Inc., 1994, Chapter 4.

To study interactions of neurons with their environment and with other neurons it is extremely important to control the adhesion and the geometry of the neurite outgrowth. It is therefore necessary to prepare surfaces with well-resolved areas to control the neurite outgrowth. In this respect, it is known to use lithographic technologies to structure the artificial surfaces of the substrate to allow chemical groups to be spatially patterned. In this connection e.g. photoresist, photopolymerisation, or deep UV light are used within the lithographic technologies.

For monitoring electrical activity of neurons, it is known to use intra-cellular methods, e.g. using glass microelectrodes or patch clamp pipettes. Although such devices can be cheaply produced, they are, as being intra-cellular devices as mentioned above, causing damages to the neurons or cells and therefore are not capable for long-term recording. Furthermore, investigation of complex systems is very difficult with these methods.

It is also known to use extra-cellular electrodes for monitoring electrical activities, e.g. by using microelectrodes or field effect transistors (FET), as described in a paper of Offenhäusser et al. "Field-Effect transistor array for monitoring neurons in culture". Biosensors and Bioelectronics 1997, Volume 12, No. 8, 819–826.

It is also known to use voltage sensitive dyes as optical probes for monitoring optical parameters directly related to neural activity, as described by Parsons et al., Biophys. Journal 1989, 56, 213. Disadvantages of the dyes are the toxicity in illumination, which also makes them unsuitable for long-term applications. Furthermore, stimulation of neurons using this method is not possible.

For an efficient investigation of a neural activity and for the above-mentioned devices it is extremely important to control the growth of cultured neurons on the substrate. A method using surfaces modified with e.g. artificial polypeptides, silanes or thiols with different end groups is only suitable for limited surfaces, like silicon or noble metal surfaces. Further and even more important, the random spatial distribution and overlapping of dendrites and axons on homogeneous substrates makes geometrically dependent studies of synaptic functions impossible.

The above-described lithographic techniques for structuring the surface, whereby the neurite outgrowth is oriented along the pattern, which is normally defined by a grid, are, on the other hand, methods requiring additional preparation steps. Furthermore, the structure has to be determined before applying the lithographic techniques and well before starting the neurite outgrowth, therefore no flexibility regarding parameters and fitting to desired applications or investigations is given. Differently structured substrates will have to be hold on stock in order to have a suitable substrate always available for the desired application.

Furthermore, as the lithographic structure is normally defined by a grid, it only allows a contact between neurons to the respective next neighbors, thereby clearly limiting the number of contacts and also limiting the speed of signal processing between neurons not being next-neighbour-neurons.

SUMMARY OF THE INVENTION

It is therefore an object of the present invention to provide a substrate structure enabling a flexible and controlled, oriented neurite outgrowth, allowing a high number of connections between the neurons, and to provide a flexible and easy performable method for manufacturing such a substrate. It is a further object of the present invention to provide a device for monitoring cell or neuron activity comprising an electronic device, achieving analog advantages and—interaction of a high intensity between neuron or cell and an electronic device, thereby ensuring a high signal-to-noise ratio.

According to the inventive method, at least one alignment layer is deposited on a basic substrate and a mono- or multilayer of a liquid crystal material is deposited on said at least one alignment layer, or a combined alignment layer is deposited on said basic substrate, thereby providing a structured surface. "Basic" substrate here means any suitable substrate being known, also combined materials or complex substrate compositions that might be used in connection with the invention, thereby no limitation is expressed by this formulation. It should be further understood by the artisan that not only neurons or nerve cells are applicable for the present invention, but all suitable cells of interest may be used.

It should be mentioned that, also preferred, it is not absolutely necessary to directly deposit the layers according to the invention onto each other, it might be also possible to apply small amounts of intermediate material inbetween.

DETAILED DESCRIPTION OF THE INVENTION

With the present invention, a self-assembly preparation of oriented surfaces will be allowed, furthermore the at least one alignment layer that orients the mono- or multilayer of liquid crystal material or the combined alignment layer provides a structured surface without the further use of lithographic techniques.

Because of the properties of the materials, the orientation of the structured surface is not fixed, but can be flexibly oriented at each time, also shortly before starting neurite outgrowth or even after neurite outgrowth has already been started.

The orientation can be controlled both in a 2 dimensional directions. i.e. parallel to the surface of the basic substrate being the most important application, and in 3 dimensional directions, i.e. additionally in a direction normal to the surface of the basic substrate. Growing of any desired neuron network can therefore be reliably controlled.

Thereby not only a high flexibility in controlling during neurite outgrowth is given, but it is also possible to manufacture substrate structures, before knowing the exact desired application, as the structure can be influenced and oriented even after manufacturing, what is absolutely impossible with substrates having a fixed grid (provided by lithographic techniques). The number of substrates to be stored, even possibly only for a short period, can therefore be limited, the manufacturing of "standard" substrates for different applications and different desired structures is simplified, e.g. only one manufacturing or machine setting is necessary, also limiting possible deviations between produced substrates due to repeated new setting and re-setting of manufacturing data.

When selecting materials in accordance with the invention, it should be noticed that neurons or cells prefer a hydrophilic surrounding rather than a hydrophobic.

Preferably the at least one alignment layer is a polymeric alignment layer, especially a polyimide. The polymeric alignment layers or polyimides have very good orienting properties, thereby being the preferred material for the inventive method.

In a preferred method a polyimide according to the following structure is used:

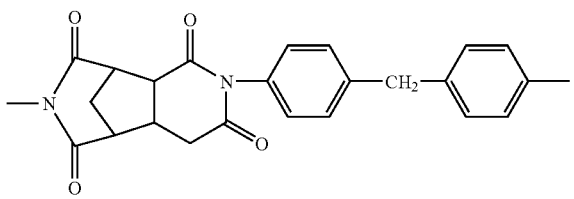

Polyimides for alignment layers are typically prepared from precursors of polyamic acids or polyamic esters. Usually the precursor polymer is first deposited and subsequently chemically or thermally converted to an insoluble polyimide.

It is also possible to use soluble preconverted polyimides. Such preconverted polyimides are commercially available, e.g. as polyimide AL1524 from JSR (Japan Synthetic Rubber).

The alignment layer is prepared in order to give it aligning properties, e.g. by rubbing it with a cloth. The liquid crystals are subsequently aligned by depositing them onto the alignment layer and letting them align at a temperature above the melting point and below the clearing point of the materials.

As liquid crystal materials preferably 4-Octyl-4-biphenyl carbonitrile (8CB) available from Merck, or 4-Pentyl-4-biphenyl carbonitrile (5CB), available from Aldrich, are used. These liquid crystals are especially useful, as their phase transition temperatures are in a range, being useful for most neurons in culture.

4-Octyl-4-biphenyl carbonitrile has its nematic phase, where the orientation of the liquid crystals is preferably controlled, between 30.2° C. and 37.1° C., whereas 4-Pentyl-4-biphenyl carbonitrile has its nematic phase between 23.7° C. and 33.7° C.

Neurite outgrowth, especially when neurons from the central nervous system (CNS) of adult vertebrate, which are a good system to study the information transfer in nervous systems, are used, is especially effective at these temperature ranges. E.g. for fish neurons the neurite outgrowth is carried out at about 23° C. and for rat neurons the growth is carried out at about 36° C. to 37° C.

Preferably the alignment layer material is dissolved and the solution is applied to the substrate by a spin coating, whereafter an annealing step is conducted.

The liquid crystal material is also preferably dissolved, e.g. in chloroform, and the solution is evaporated onto said alignment layer.

Thereby a reliable structure with a constant and desired covering amount of each layer material is achieved.

An example for a preferred preparation method according to the invention is given in the following:

250 µl of a polyimide solution in γ-butyrolacton is spin coated on a glass substrate and annealed. Spin coating conditions are: 1000 rpm for 4 s, 3500 rpm for 30 s. Annealing conditions are: 80° C. for 15 min. and 250° C. for 60 min.

The polyimide was rubbed under the following conditions: material of cloth is rayon, speed of rubbing cylinder is ω=1.400 rpm, table speed is v=2.2 mm/s, the process was repeated two times, uni-directionally.

To form a liquid crystal monolayer, 250 µl of $5 \times 10^{-5}$ molar solution in chloroform are evaporated on top. To form a liquid crystal multilayer comprising about 10 layers, 250 µl of $2 \times 10^{-4}$ molar solution in chloroform are evaporated on top.

The monolayer concentration was calculated by using the geometrical dimensions of 4-Octyl-4-biphenyl carbonitrile (8CB).

The combined alignment layer that can be used instead of the separated alignment layer and liquid crystal layer, preferably comprises polymeric material that has been selected from the group comprising polyester, polypeptide, polyacrylamide, polyvinyl alcohol, polyacrylate, polymethacrylate, polyurea and polyamide. In this context "polymeric material" means material, in which the majority of molecules are polymers. In one embodiment the polymeric material is liquid crystalline, in another embodiment amorphous, in a third embodiment the polymeric material comprises both, liquid crystalline and amorphous elements. The term "element" in this context is meant to describe a set of molecules, the molecules having the same or a different structural formula, the unifying concept being that all molecules within an element have the same behaviour with respect to the "crystallinity" of the element. In one embodiment it is preferred that the polymeric material has at least one azobenzene chromophore covalently attached. The term "said polymeric material has at least one azobenzene chromophore covalently attached" is meant to include the options that all, some or only a few of the polymers present in the polymeric material have azobenzene chromophores covalently attached. In one embodiment the azobenzene chromophore is preferably represented by the formula:

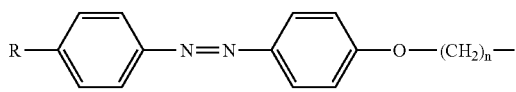

where R is selected from the group comprising $CN$, $NO_2$, $OCH_3$, H, $CH_3$, $(CH_2)_3CH_3$, F, Cl, Br, $CF_3$, $C_6H_5$, $O(CH_2)_2OCH_3$ and $(CH_2)_5CH_3$ and where n is selected from the range: $0 \leq n \leq 12$. In one embodiment the polyester is a sidechain liquid-crystalline polyester, preferably an azobenzene sidechain liquid-crystalline polyester. Such azobenzene sidechain liquid-crystalline polyesters can, for example, be prepared by different combinations of ester precursors and azobenzene diols. Such polyesters can be described in terms of a simple nomenclature, the Pnxm-system coined by S. Hvilsted et al., 1998, Tr. J. of Chemistry, 22, 33–45, in which n represents the number of methylene groups in the flexible sidechain spacer and x refers to the para-substituent, where a=CN, b=$NO_2$, c=$OCH_3$, d=H, e=$CH_3$, f=$(CH_2)_3CH_3$, g=F, h=Cl, i=Br, j=$CF_3$ and k=$C_6H_5$ on the azobenzene. m reflects the number of methylene groups in the acidic part of the main chain. In one preferred embodiment said azobenzene sidechain liquid-crystalline polyester is selected from the group comprising P6a12, P6a10, P10a10, P8a12 and P10a12. Especially the polyester characterized by six methylene groups in the flexible spacer, a cyanoazobenzene chromophore, and 12 methylene groups in the acidic part of the main chain, known as P6a12, is used. The chemical formula for P6a12 is poly(2-{6-[4-4-cyanophenylazo)phenoxy]-hexyl}-1,3-propylenetetradecanedioate. But, also P6a10, P8a10, P10a10, P8a12 or P10a12 or similar materials may be used.

In one embodiment the polypeptide is selected from the group comprising polyglutamate, polyproline and polyornithine, and preferably from the group comprising

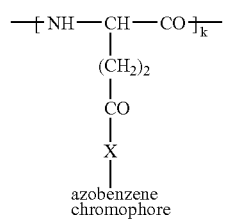

-continued

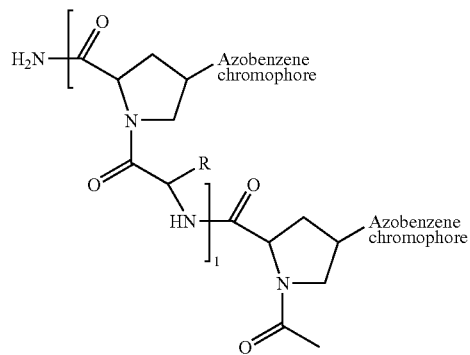

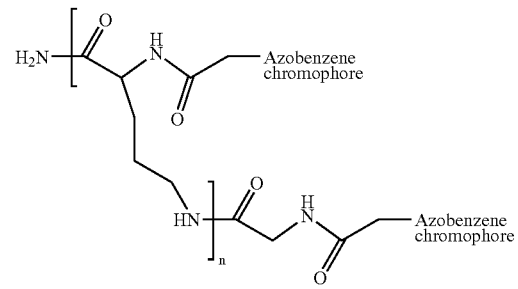

where X is selected from the group comprising NH and O, where the azobenzene chromophore is defined as in claim 15, and where k, n and l are selected from the range: $1 \leq (k$ or l or $n) \leq 500$.

In one embodiment the polyacrylamide is selected from the group comprising

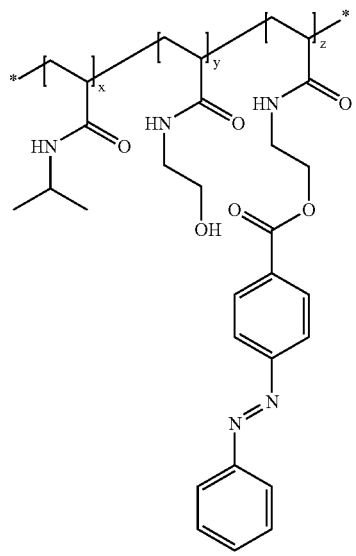

-continued

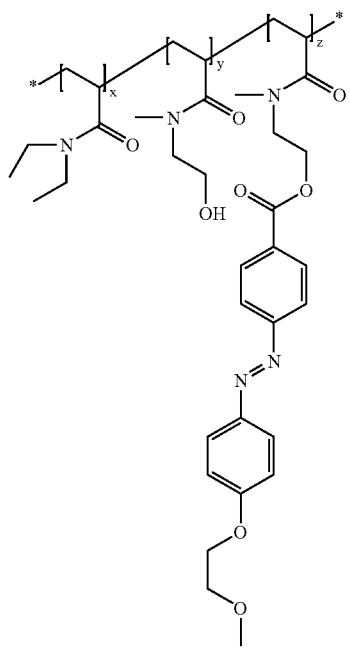

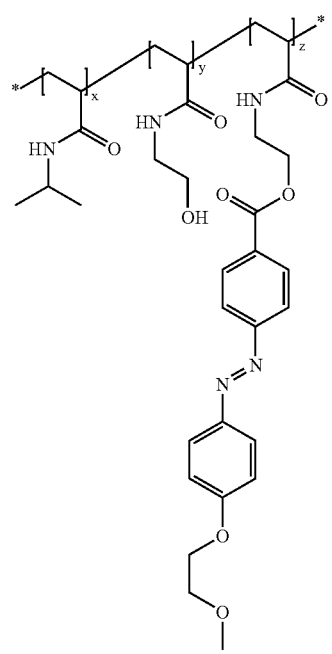

where x is selected from the range: $0.2 \leq x \leq 1$, y is selected from the range: $0.1 \leq y \leq 1$, z is selected from the range: $0.005 \leq z \leq 0.025$, and $x+y+z=1$ for all combinations of x, y and z.

In one embodiment the polyvinyl alcohol is selected from the group comprising

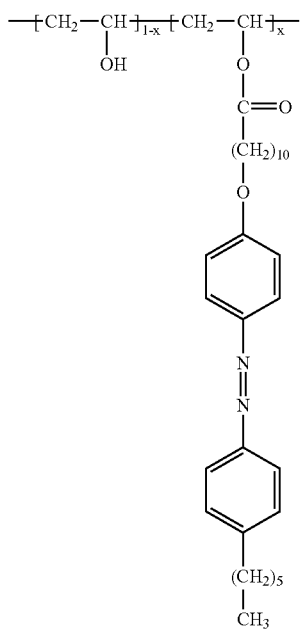

where x is selected from the range: $0.2 \leq x \leq 0.6$.

In one embodiment the combined alignment layer that can be used instead of the separated alignment layer and liquid-crystal layer, comprises monomeric material. In this context "monomeric material" means material in which the majority of molecules are monomers. In one embodiment the monomeric material is liquid crystalline, in another embodiment amorphous, in a third embodiment there is a mixture of monomeric material comprising both liquid crystalline and amorphous elements. The term "element" in this context is meant to describe a set of molecules, the molecules having the same or a different structural formula, the unifying concept being that all molecules within an element have the same behaviour with respect to the "cristallinity" of the element. In one embodiment the combined alignment layer comprises at least one type of azosilane. The azosilane preferably is selected from the group comprising

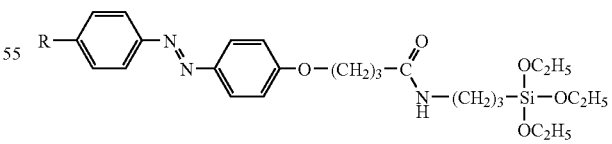

where R is selected from the group comprising CN, $NO_2$, $OCH_3$, H, $CH_3$, $(CH_2)_3CH_3$, F, Cl, Br, $CF_3$, $C_6H_5$, $O(CH_2)_2OCH_3$ and $(CH_2)_5CH_3$.

The most important criterion which any of the above materials have to fulfill is the low toxicity towards cells, the capability of undergoing many cycles of switching, the capability of undergoing switching under physiological or nearly physiological conditions, preferably 36.5° C., in buffered aqueous solution.

Such a combined layer can easily be deposited by dissolving the material, e.g. in chloroform, and spin coating it on the basic substrate or by Langmuir-Blodgett-technique, wherein in the latter case the substrate directly has an orientation by preparation. In both cases an optical switching or orientating can be conducted after deposition. Especially for such an optical switching and directing of the oriented surface, such a combined layer is very preferable. An optical switching of the structured surface has, dependent on the cells, less influence to the neurons or cells in comparison with an electrical switching, which is important, in case switching is conducted when the neurons or cells are already put on the substrate structure, especially during neurite outgrowth.

The above-described substrates produced by the inventive method can be used as artificial surfaces for culturing all kinds of cells and neurons, especially for culturing hippocampus neurons of embryonic rats. It is also possible to use cell-lines of neuronal cells. Alternatively non-neuronal cell-lines can be used that are being differentiated into neurons in the course of the experiment by adding appropriate amounts of differentiation inducing agents like retinoic acid. The cells are placed on the alignment layer or combined alignment layer in the medium at a density preferably in the range of 2.000–20.000 cells/100 $mm^2$–900 $mm^2$ of substrate.

As mentioned above, one of the most important advantages of the inventive method and the respective substrate structure is the controllability of the structured surface.

The orientation of the liquid crystal can be controlled by external means, especially by an electric field or also by electromagnetic irradiation, e.g. applied by laser means. Depending on the cells or neurons, electromagnetic irradiation may be preferred, because it will less influence the cells or neurons, as explained above.

As a source of electromagnetic radiation, a laser, for example, can be used. There is no restriction to the laser source in view of the invention, so conventional and well-known lasers can be taken. One possible laser source is a YAG laser, e.g. a frequency doubled YAG laser, lasing at a wavelength of 532 nm with a power of 35 mW. Another suitable laser would be a HeCd laser, linearly polarized at a wavelength of 442 nm and a preferred power of about 100 mW. Further an Argon-ion laser can be employed, lasing with a wavelength of 488 nm. It is obvious to the expert that also other lasers might be used, as long as the inventive method can be realized, and it will be no problem to an artisan to suit power and wavelength as well as apparatus setup to the materials used.

It is also possible to use a laser, e.g. a He—Ne laser, as read-out means, in order to check orientation of the liquid crystal material, controlled by above mentioned control laser. Power of such a laser would be remarkably less in comparison with the control laser, in order not to influence induced orientation.

The orientation switching of liquid crystal material layers is preferably conducted at a temperature, at which the crystal material is in its nematic phase. But, also a switching of the material in the smectic phase will be possible. Furthermore switching between cis- and trans-configurations and vice versa will be possible. The respective phase will be chosen to be in accordance with the application, the used neurons or cells etc.

Thereby with simple and reliable external means the orientation of the structured surface and thereby the direction of neurite outgrowth can be controlled and changed also during the growth process. It is thereby possible to both control, which neurons are connected, as a specific angle of orientation will lead to a connection of specific neurons and to a directed neurite outgrowth.

Furthermore, it is possible not only to connect next neighbors, but to build up a very complex neural network with multiple connections, yielding to a faster signal processing. This is an important criterion for an application e.g. in the field of data storage or data acquisition.

In this respect, it should be noticed that the control of the neurite outgrowth can be achieved both in 2 dimensions as well as in 3 dimensions, as already mentioned above, although normally a 2-dimensional arrangement will be desired and sufficient.

An inventive substrate structure for neurite outgrowth comprises a basic substrate, an alignment layer deposited on said substrate and a mono- or multilayer of liquid crystal materials, deposited on said alignment layer, or a combined alignment layer. The basic substrate is preferably a glass substrate. Examples of substrates are microscope slides, haemacytometer slides, silica, arrays of FETs, electrode structures on silica or glass.

The inventive substrate structure is very flexible with respect to different applications and provides an ideal surface for a neurite outgrowth. It has a non-toxic interface, a good long-term stability in physiological conditions and it provides a good adhesive contact. To improve the adhesion of cells, in one embodiment the alignment layer or combined alignment layer is coated with at least one type of protein, preferably a matrix protein, e.g. laminin and/or an adhesive cell-surface protein, e.g. fibronectin.

As explained above, a flexibly usable structured surface is achieved, the orientation of the structured surface can be controlled by external means, especially by applying an electric field or electromagnetic irradiation. The neurite outgrowth can be controlled easily and effectively and a highly complex and connected neural network can be built up in 2 and in 3 dimensions on the basis of the inventive substrate structure.

The basic substrate may be covered with a conductive layer, preferably an ITO-(Indium-Tin-Oxide) or a FTO-(Fluoride-Tin-Oxide) layer, which can be used as an electrode device for switching and controlling neurons or cells. Preferably a comb structure of said conductive layer is deposited on the basic structure, providing a homogenous field over the whole 2 dimensional area. A sandwich structure may also be provided.

Preferably, but not limited to, the thickness of the alignment layer is selected to be in the range from 10 to 200 nm, preferably about 100 nm, and the thickness of the liquid crystal layer is selected to be in the range of from 10 to 150 nm, preferably about 100 nm. The multilayer thickness of the liquid crystal layer has to be sufficient to be switchable. The combined alignment layer comprising liquid crystal materials preferably has a thickness of 20 to 350 nm, especially of 200 nm.

A device for monitoring cell or neuron activity according to the present invention comprises a substrate, at least one electronic device, at least one neuron/cell in close proximity of the at least one electronic device, wherein said neuron/cell is coupled to the electronic device, so that an activity of the neuron will influence the electronic device and produces a measurable reaction and vice versa, wherein an alignment layer is provided on said substrate and a mono- or multilayer of liquid crystal material is provided on the alignment layer, or a combined alignment layer is deposited on said substrate.

As explained above, the flexibility for creating or building a neural network or architecture, being extremely important for such a monitoring device, is achieved by the structure and the controllability of the structural surface.

A monitoring device according to the present invention can be flexibly but easily manufactured. Furthermore, a very good adhesive contact and a close physical and non toxic interfacing is achieved. It will provide a high signal-to-noise-ratio and a high sensitivity, when monitoring the neurons or cells of the respective network. Furthermore a stimulation of the neurons using the electronic device is possible.

The inventive substrate and/or device with the high flexibility and the potential for the building of a highly complex and connected 2- or 3-dimenaional neural network enables various possibilities for information processing by artificial neuronal networks, for sensing in medical applications or for a better understanding of brain functions and mechanisms. It is also possible to use such a device as a model system to learn about brain functions and designable electronic circuits. Additionally it will be used as a model or a development tool for software design, being comparable with neural network functions.

Further features and advantages of the present invention will be apparent from the description of a specific embodiment in connection with the drawings, wherein

DETAILED DESCRIPTION OS THE DRAWINGS

Figure 1:
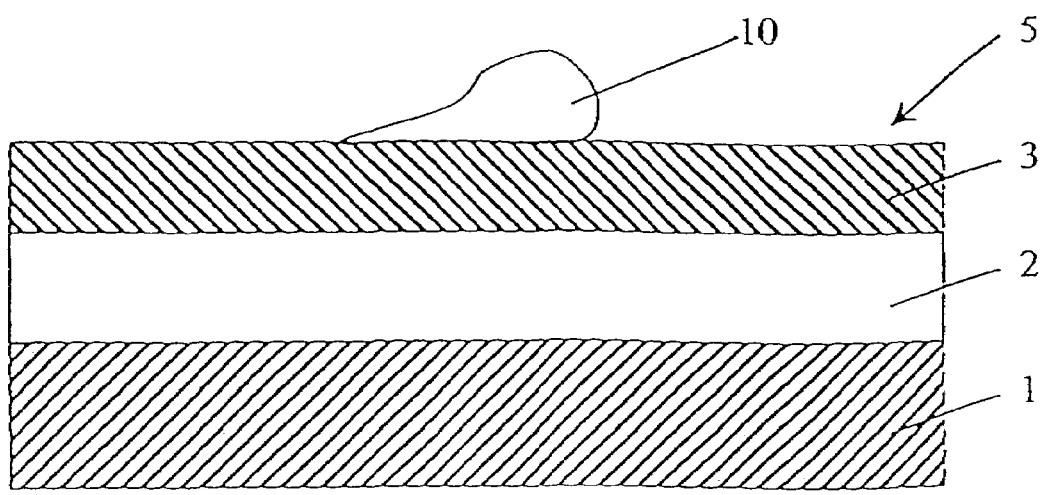
FIG. 1 schematically shows an embodiment of a substrate structure according to the invention with a neuron, and FIG. 2 schematically shows the interconnected structure of an embodiment of a device for monitoring cell or neuron activity according to the present invention.

FIG. 1 shows the structure of an embodiment of the inventive substrate 5, comprising a basic glass substrate 1 having a thickness of 1.1 mm, a polyimide layer 2 having a thickness of about 100 nm and a liquid crystal layer 3 having a thickness of 15–20 nm for a monolayer and a thickness of 150–200 nm for a multilayer.

As polyimide material the pre-converted polyimide AL 1524, available from the company "Japan Synthetic Rubber", is used.

The liquid crystal layer 3 is a mono- or multilayer of 4-Octyl-4-biphenyl carbonitrile (8CB), available from the company Merck. On the oriented liquid crystal layer, a hippocampal neuron 10 is positioned. The hippocampal neuron is e.g. of embryonic rat, but it should be noticed that also a CNS neuron, e.g. of adult goldfish, or cardiac mycocytes, as has been experimentally shown, or any other neuron or cell can be used. Beside differentiated primary cell cultures, brain slices or permanent cell lines can be used, which can—by addition of appropriate agents, e.g. retinoic acid,—behave neuron like.

Only for completion, it should be noted that instead of the layers 2, 3 a combined alignment layer can be provided.

Neuron-like characteristics as synaptic contacts can be adapted by cells from cell-lines being commercially available. This has the advantage that the characteristics of different cell culture experiments are comparable to each other.

Experiments with hippocampal neurons of embryonic rats both on oriented and not oriented liquid crystal material have shown a much better performance regarding neurite outgrowth on oriented surfaces, as it is a goal of the present invention.

A very close physical interfacing could be achieved between the hippocampal neuron 10 and the substrate structure 5 or the liquid crystal layer 3 respectively. This is one of the most important requirements or conditions especially for a monitoring device, as schematically shown in FIG. 2, in order to ensure good interaction between neuron and electronic device and a good signal-to noise-ratio.

Figure 2:
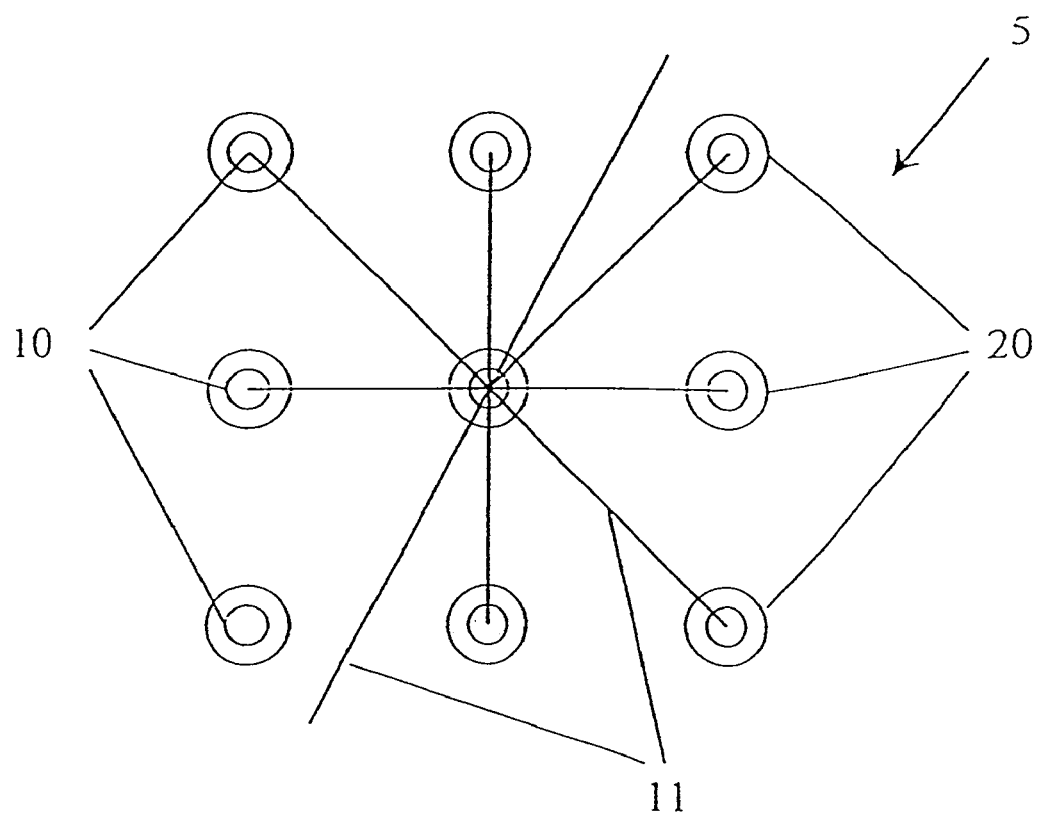

FIG. 2 schematically shows a structure of an embodiment of a device for monitoring cell or neuron activity according to the invention. For simplicity, only 9 hippocampal neurons 10 in a 2-dimensional arrangement and only some selected connections are shown, but it should be noticed that actually a complex 2-dimensional structure of hippocampal neurons is realized in this embodiment. All neurons are coupled with the field effect transistors (FET).

In a substrate structure 5 there are field effect transistors 20 incorporated. On each field effect transistor 20, a neuron 10 is deposited on the non-metallized gate of FET.

The neurons 10 are again hippocampal neurons and they are connected by dendrites and axons 11, again shown only schematically.

As can be seen, connections 11 are not only between next neighbor neurons, but also to more distant neighbors, thereby allowing a highly connected network, yielding to fast signal processing.

Thereby a system being much closer to real brain functions and structure is realized. Both a reliable measurement or monitoring and/or a stimulation of single or multiple neurons 10 is possible, enabling a huge variety of investigation of brain and neuron functions and interactions.

In this figure, only one possibility of connection and neurite outgrowth could be shown, but it should be understood that because of the controllability of the orientation of the liquid crystal layer 3, every desired connection structure can be achieved. It is even possible to avoid next neighbor connections, if desired, and to have connections only between neurons being located from each other with a minimum distance.

Figure 3:
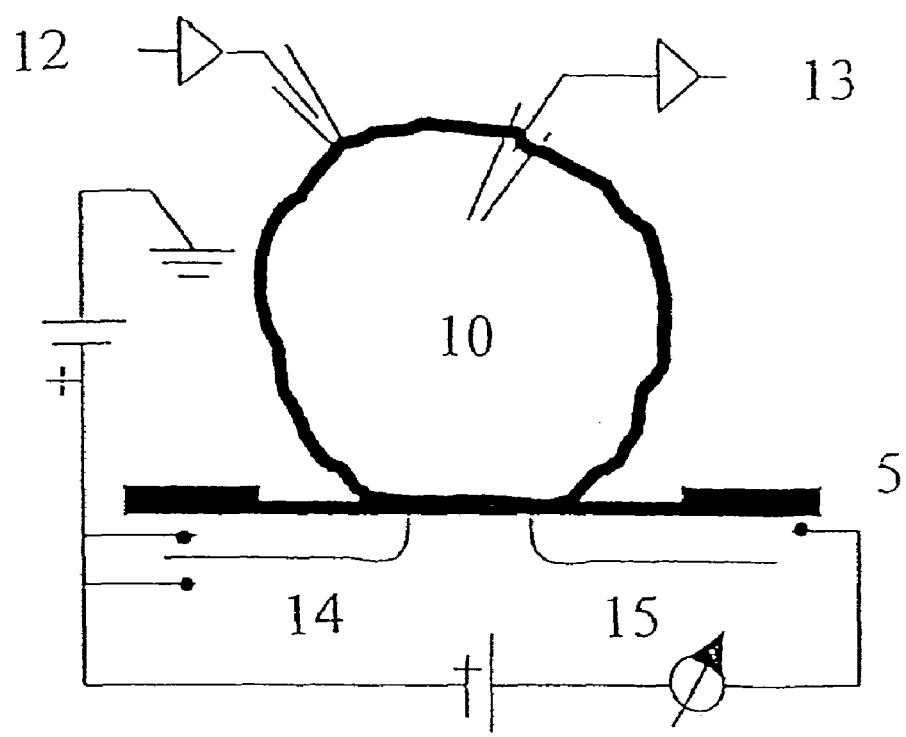
FIG. 3 schematically shows a collection of possible techniques for monitoring cell or neuron activity according to the present invention.

FIG. 3 shows possible techniques for monitoring cell or neuron activity according to the invention. The neuron 10 has been cultured on a non-metallised gate of a field effect transistor comprising a source 14 and a drain 15 and is attached to a patch clamp electrode 12 or a microelectrode 13.

As mentioned before cells can be neurons from various origins or cells from permanent cell lines which are differentiated into neurons in the course of the experiment. The following section describes in an exemplifying manner the cultivation and growth of cells that can be used for the purposes of the invention:

For hippocampal neurons, Neurobasal media supplemented with B27 can be used, and the cells are plated at about 5,000 cells/cm$^2$.

As a permanent cell line for example the P19 cell line (ATCC number: CRL-1825) can be used.

The P19 cells can normally be cultured in alpha MEM, supplemented with:
1) Calf serum 7.5% (v/v), heat inactivated at 56.0° C. for 30 minutes.

2) Fetal calf serum 2.5% (v/v), heat inactivated at 56.0° C. for 30 minutes.
3) 1% non essential amino acids.

Optionally antibiotics can be used to prevent microbial growth.

They are routinely passaged every 24–48 hours according to the following protocol:
1) Aspirate media and rinse monolayer twice with calcium- and magnesium-free PBS (phosphate buffered saline solution) containing 0.8% NaCl, 0.02% KCl, 0.02% $KH_2PO_4$ and 0.115% $Na_2HPO_4$ (pH 7.4).
2) 0.025% Trypsin in 1 mM EDTA all in PBS. Incubate at room temp. for few minutes until cells detach from surface by gentle tapping.
3) Wash cells from surface by trituration.
4) Transfer cells to 5 ml of serum containing growth media in 15 ml conical flask.
5) Centrifuge at 300 rpm for 5 minutes.
6) Aspirate media from tubes and re-suspend in 5 ml fresh growth media.
7) Break up clumps of cells by trituration.
8) Count cells and plate at approximately 10,000 cells/cm². Spread cells evenly.
9) Passage cells when confluent, 1 every 24–48 hours.

They can be differentiated into neurons according to the following protocol:
1) Trypsinize cells as in routine passage and plate in 100 mm TC grade dish (10 ml).
2) Dilute retinoic acid (RA) to $3\times10^{-5}$ M by adding 30 μl of stock to 0.97 ml medium. Add 100 μl of this to the freshly plated cells so use final conc. of $3\times10^{-7}$ M. Turn lights off in flow hood during this process because retinoic acid is photo-sensitive.
3) Incubate at 37.0° C. for 48 h.
4) Trypsinize the monolayer as for passage, count and add $5\times10^5$ cells to 60 mm bacterial grade petri dish, add 50 μl of freshly diluted RA as above.
5) Allow cells to aggregate in suspension for 24 hrs.
6) Transfer aggregates to 15 ml flask and centrifuge.
7) Aspirate and wash once with PBS.
8) Repelled and add 0.5 ml EDTA-trypsin. Agitate the tube to re-suspend aggregates.
9) Incubate for 4 minutes at room temperature and then add to 4.5 ml growth media.
10) Break up aggregates and then plate.
11) Change media after 24 hrs and then every 48 hrs.

Alternatively in serum-free medium they can be differentiated according to the following protocol:
1) Trypsinize as for passage.
2) After spinning, re-suspend in 5 ml serum free media.
3) Count cells and add $2–3\times10^6$ cells to 10 ml of serum media in TC dish.
4) Incubate for 48 hrs. Cells will aggregate that loosely attach to the dish.
5) Trypsinize (0.5 ml Trypsin EDTA).
6) Add 4.5 ml α-MEM plus serum and triturate to produce single cell suspension.
7) Spin and re-suspend in 5 ml serum free media.
8) Count and re-aggregate by adding $2–3\times10^5$ cell/ml of serum free suspension to bacterial grade petri dish.
9) Incubate for 48 hrs.
10) Plate aggregates on laminin coated substrates.
11) Maintain cells in serum free, changing media every 2–3 days.

These cultures will survive for up to 12–16 days. However, long term cultures can be achieved by maintaining cells in α-MEM plus serum for the first 6 days, and then switching to serum free media, changing media every 48 hours. This allows some non-neuronal cells to survive. Cells cultured this way can be maintained for up to 57 days.

For the serum free differentiation Neurobasal media from GIBCO (Cat. No. 21103), again supplemented with B27 (Cat. No. 17504) can be used.

In addition to the dissociated primary cell culture, also brain slices with a thickness in the order of e.g. 250 μm can be used.

In such a system the neurons move out of the brain slice. If the slices are placed on a patterned substrate, the neurons will move along this pattern and perform neurite outgrowth on it. To provide an example, the following media can be used:

Brain Slices: Sequential use of the following solutions:

Bottle 1

HBSS containing Antibiotics (10 ml of Antibiotics in 500 ml of HBSS)

Bottle 2

HBSS containing Antibiotics and Glutamine (10 ml of Antibiotics and 15 ml of Glutamine in 500 ml of HBSS)

Bottle 3

F10 HAMS containing approx 5% of FCS, Antibiotics and Glutamine (25 ml of FCS in 400 ml of F10 HAMS plus 8 ml of Antibiotics and 12 ml of Glutamine)

Bottle 4.

F10 HAMS containing 20–25% FCS and Glutamine (for initial plating)

(100 ml of FCS in 400 ml of F10 HAMS plus 12 ml of Glutamine)

Bottle 5 (Optional) Could Use Ara-C Instead

F10 HAMS serum free, with Glutamine only (For Day 2 onwards)

(12 ml of Glutamine in 400 ml of F10 HAMS)

If necessary, the adhesion of the neurons can be improved by an additional coating, e.g. laminin.

The features of the present invention disclosed in the specification, the claims and/or in the accompanying drawings, may, both separately and in any combination thereof, be material for realizing the invention in various forms thereof.

The invention claimed is:

1. A substrate structure for biological neurite outgrowth, with the capability of undergoing many cycles of switching, comprising: a) a basic substrate and b) an alignment layer on said basic substrate, with a mono- or multi-layer of liquid crystal material on said alignment layer, or a combined alignment layer on said basic substrate, wherein said combined alignment layer includes a liquid crystal, and said combined alignment layer further comprises polymeric material selected from the group consisting of polyester, polypeptide, polyacrylamide, polyvinylalcohol, polyacrylate, polymethacrylate, polyurea and polyamide, or at least one type of azosilane; wherein said substrate structure for biological neurite outgrowth has at least one biological neuron on top of said mono- or multi-layer of liquid crystal material, or on top of said combined alignment layer which includes a liquid crystal; and wherein the orientation of the alignment layer or the combined alignment layer, and thereby the direction of biological neurite outgrowth, is controllable and changeable during the growth process of the biological neuron.

2. The substrate structure according to claim 1, wherein said basic substrate comprises a glass substrate.

3. The substrate structure according to claim 2, wherein said glass substrate is covered with a conductive layer or an electrode arrangement.

4. The substrate structure according to 3, wherein said at least one alignment layer is a polyimide.

5. The substrate structure according to claim 4, wherein said polyimide is represented by the following repeat unit:

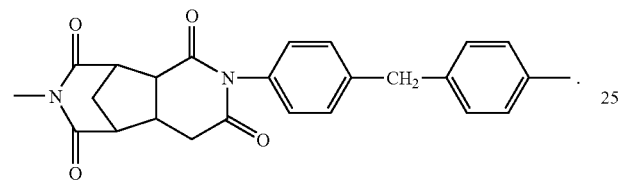

6. The substrate structure according to claim 3, wherein said at least one alignment layer is a polymeric alignment layer.

7. The substrate structure according to claim 1, wherein said polyester is a side chain liquid-crystalline polyester.

8. The substrate structure according to claim 7, wherein said side chain liquid-crystalline polyester is an azobenzene side chain liquid-crystalline polyester.

9. The substrate structure according to claim 8, wherein said azobenzene side chain liquid-crystalline polyester is a Pxnm-polyester selected from the group consisting of P6a12, P6a10, P8a10, P10a10, P8a12 and P10a12, wherein x is a para-substituent, n is the number of methylene groups in a flexible side chain spacer and m is the number of methylene groups in an acidic part of a main chain.

10. The substrate structure according to claim 1, wherein that said polymeric material has at least one azobenzene chromophore covalently attached thereto.

11. Substrate structure according to claim 10, wherein said azobenzene chromophore is represented by the formula:

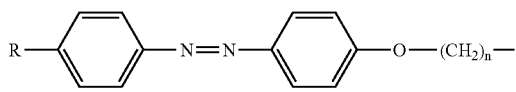

wherein R is selected from the group consisting of CN, $NO_2$, $OCH_3$, H, $CH_3$, $(CH_2)_3CH_3$, F, Cl, Br, $CF_3$, $C_6H_5$, $O(CH_2)_2OCH_3$ and $(CH_2)_5CH_3$, and wherein n is selected from the range: $0 \leq n \leq 12$.

12. The substrate structure according to claim 1, wherein said polypeptide is selected from the group consisting of polyglutamate, polyproline and polyornithine.

13. The substrate structure according to claim 1, wherein said polypeptide is selected from the group consisting of:

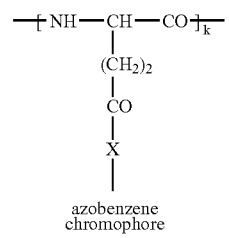

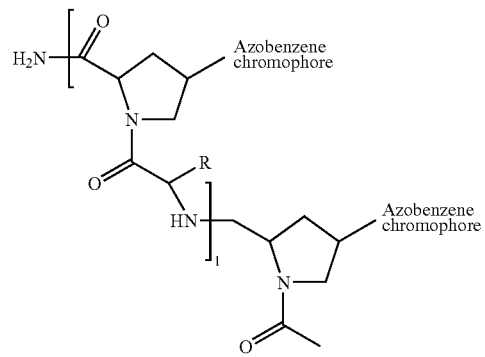

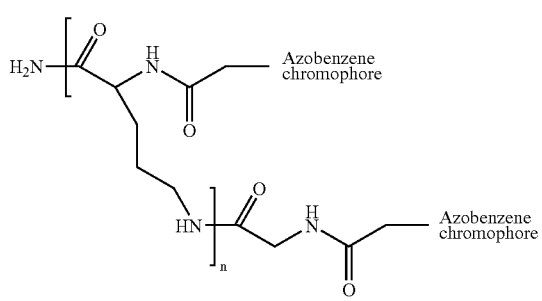

wherein X is selected from the group consisting of NH and O, and wherein k, n and l are selected from the range: $1 \leq (k$ or $l$ or $n) \leq 500$.

14. The substrate structure according to claim 1, wherein said liquid crystal material is 4-Octyl-4-biphenyl carbonitrile and/or 4-Pentyl-4-biphenyl carbonitrile.

15. The substrate structure according to claim 1, wherein said at least one alignment layer has a thickness from 10 to 200 nm.

16. The substrate structure according to claim 1, wherein said at least one alignment layer has a thickness of about 100 nm.

17. The substrate structure according to claim 1, wherein said liquid crystal material has a thickness from 10 to 150 nm.

18. The substrate structure according to claim 1, wherein said liquid crystal material has a thickness of about 100 nm.

19. The substrate structure according to claim 1, wherein said polyacrylamide is selected from the group consisting of:

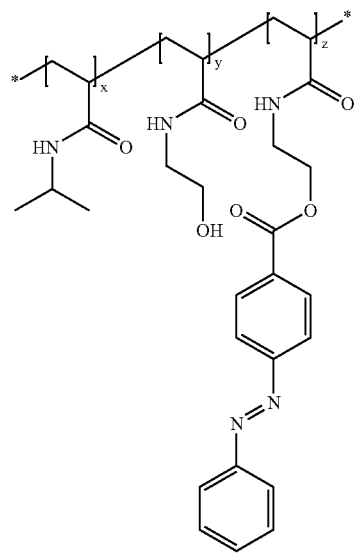

-continued

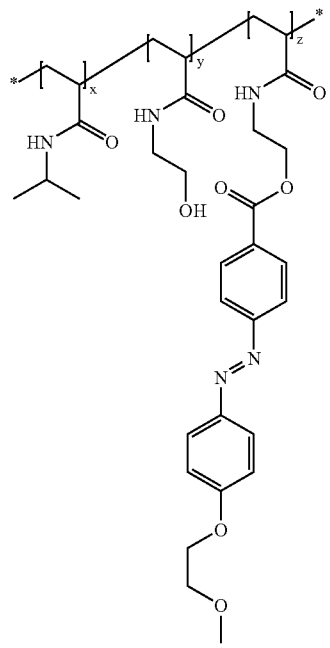

wherein x is selected from the range: $0.2 \leq x \leq 1$, y is selected from the range: $0.1 \leq y \leq 1$, z is selected from the range: $0.005 \leq z \leq 0.025$, and $x+y+z=1$ for all combinations of x, y and z.

20. The substrate structure according to claim 1, wherein said polyvinyl alcohol is selected from the group consisting of:

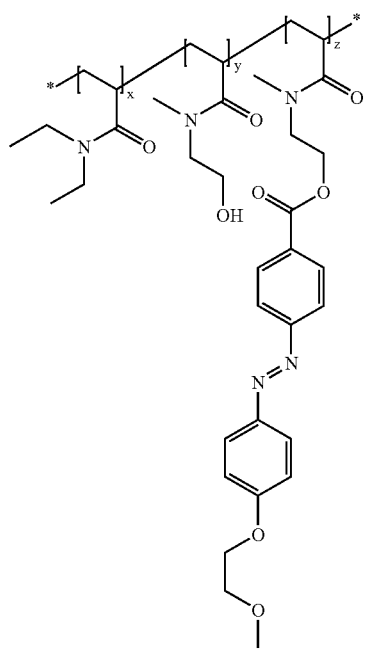

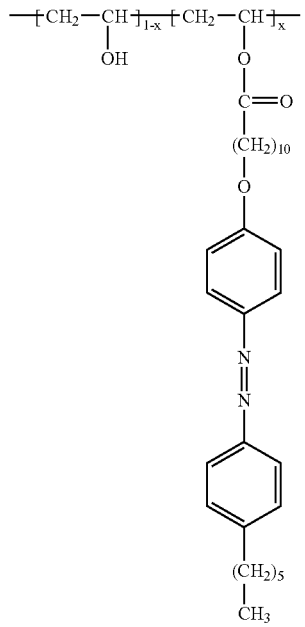

wherein x is selected from the range: $0.2 \leq x \leq 0.6$.

21. The substrate structure according to claim 1, wherein said at least one type of azosilane is of the formula:

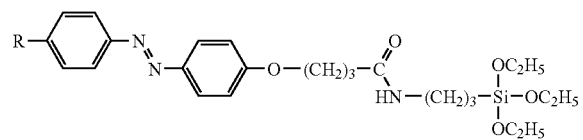

wherein R is selected from the group consisting of CN, $NO_2$, $OCH_3$, H, $CH_3$, $(CH_2)_3CH_3$, F, Cl, Br, $CF_3$, $C_6H_5$, $O(CH_2)_2OCH_3$ and $(CH_2)_5CH_3$.

22. The substrate structure according to claim 1, wherein said combined alignment layer has a thickness of 20 nm to 350 nm.

23. The substrate structure according to claim 1, wherein said combined alignment layer has a thickness of 200 nm.

* * * * *